United States Patent [19]

Ellis

[11] 4,288,402

[45] Sep. 8, 1981

[54] ACID FIELD TEST KIT FOR REFRIGERATION OILS CONTAINING A LEAK DETECTOR

[75] Inventor: Leonard C. Ellis, Chesapeake, Va.

[73] Assignee: Virginia Chemicals Inc., Portsmouth, Va.

[21] Appl. No.: 33,240

[22] Filed: Apr. 25, 1979

[51] Int. Cl.$^3$ .............................................. G01N 33/28
[52] U.S. Cl. ................................ 422/61; 23/230 HC; 252/408
[58] Field of Search ........ 422/61; 23/230 R, 230 HC, 23/230 L; 252/408

[56] References Cited

U.S. PATENT DOCUMENTS

| | | | |
|---|---|---|---|
| 3,193,356 | 7/1965 | Smith et al. ....................... | 23/230 R |
| 3,259,463 | 7/1966 | Feasley et al. ................. | 23/230 HC |
| 3,510,260 | 5/1970 | Krawetz et al. .................. | 23/230 R |
| 3,808,149 | 4/1974 | Ellis et al. .................. | 23/230 HC X |
| 3,811,837 | 5/1974 | Hoffman ........................ | 23/230 HC |

Primary Examiner—Arnold Turk
Attorney, Agent, or Firm—Depaoli & O'Brien

[57] ABSTRACT

A field test kit which uses a single vial is useful in testing acidity in refrigeration oils contaminated with a colored leak detector. This vial contains a pre-measured indicator solution and has sufficient additional volume that the test oil can be added directly to the indicator solution and accurately measured within the vial. After shaking, the mixture quickly separates into two phases. The color of the bottom phase indicates whether or not the acidity of the refrigeration oil exceeds 0.05 acid number.

29 Claims, No Drawings

ACID FIELD TEST KIT FOR REFRIGERATION OILS CONTAINING A LEAK DETECTOR

BACKGROUND OF THE INVENTION

1. Field of the Invention

This invention relates to test kits for detecting acidity in oils and particularly relates to field test kits for detecting acidity in refrigeration oils which are contaminated with a leak detecting component.

2. Review of Prior Art

In the refrigeration industry, lubricating oils are tested for acidity as an indication of suitability for continued use and as a means for detecting contamination of the entire refrigeration system. Such tests are set forth in ASTM D664-58 and ASTM D974-64, but the requirements of D664-58 for laboratory equipment makes this procedure unsuitable for field testing, and testing according to D974-64 is not satisfactory with dark colored samples of refrigeration oils because the color changes that are produced by a color indicator such as p-naphtholbenzein solution are obscured by the color of the sample, making it difficult to estimate color changes with sufficient precision.

Acid field test kits for use on refrigeration and airconditioning systems have been developed to meet this need and are currently designed to show whether or not the acidity of the refrigeration oil is above an acid number of 0.045 to 0.05, as determined by the color produced by an acid/base indicator in the test kit. New refrigeration oils intended for use in refrigeration systems generally have an acid number of from 0.01 to 0.02 when tested according to conventional ASTM test methods. Such an acid number represents the quantity of base, expressed in milligrams of potassium hydroxide, that is required to titrate all acidic materials in a 1-gram sample of the oil that are dissociated sufficiently to react to the KOH. According to experience, when a refrigeration oil develops an acid content which corresponds to an acid number of from 0.05 to 0.07, it should be replaced with new oil.

There are four acid field test kits which are now in popular use for testing refrigeration and air-conditioning systems. Two of these four field test kits produce a homogeneous mixture after shaking, and two produce a mixture that separates into two phases, the aqueous bottom phase containing the telltale color. The two-phase kits are based upon the method disclosed in U.S. Pat. No. 3,510,260 for forming an aqueous acid solution as an immiscible bottom phase, in which the acidic components are dissolved, with the oil as the top phase. When testing dark oils with a homogeneous-type kit, the color change is obviously likely to be masked. When using the two-phase method, the color change of an indicator solution, such as a one percent solution of phenolphthalein in ethanol, can become easily observable even with a dark oil when the aqueous phase turns from colorless to pink or red. However, if a red-colored leak detector is present as a component of the oil, the color change can be entirely obscured.

For example, when the refrigeration oil is contaminated with a leak detector such as the highly colored additive marketed by E. I. Dupont de Nemours and Company as Dytel, the color of the homogeneous mixture is distorted and the test results are no longer reliable. It is believed that the alkylanilino-substituted anthraquinone dyes in U.S. Pat. No. 3,770,640 are sold under the mark, Dytel. Other leak detectors are disclosed in U.S. Pat. No. 3,370,013 as organic dye compounds such as methyl derivatives of azobenzene-4-azo-2-naphthol, phenyl-azo-2-naphthol and methyl derivatives of azo-benzene-4-azo-2-naphthol, phenyl-azo-2-naphthol, and p-diethylaminoazobenzene.

One homogeneous-type device, identified as "TKO ACID TEST KIT," is simplest to use. It employs a single vial, having a capacity of two fluid ounces, containing a purple mixture of alcoholic potassium hydroxide, an acid-base indicator and a solvent mixture comprising benzene and ethyl alcohol or, preferably toluene and isopropanol. By adding refrigeration oil to the mold line on the neck of the test vial, the correct amount of oil that corresponds to the amount of potassium hydroxide is obtained. The vial need be shaken for only a few seconds after addition of the refrigeration oil sample to produce a homogeneous mixture, with no transfers and no delay for separation into distinct phases. If the test sample has an acid number less than 0.045, the color of the mixture in the shaken vial remains purple. If the oil sample has a borderline acidity, the color becomes orange, indicating that changing the oil is desirable. If the oil is definitely too acidic, the color becomes yellow, indicating that the oil must be changed. Unfortunately, if a red leak detector is present as a component of the refrigeration oil, the results are unreliable.

Another test kit of the homogeneous type is identified "as 'ONE TIME ACID TEST KIT' and consists of a two-fluid ounce vial containing an acid-base indicator in a benzene-ethyl alcohol media (reddish-orange in color). A second vial of approximately 0.5 fluid oz., with a capacity for 15.5 g of fresh refrigeration oil, contains an alcoholic potassium hydroxide solution in benzene. According to the test procedure, the contents of the small vial are emptied into the larger vial producing a violet color. The small vial, which also serves as the measuring vial, is then filled with the test oil and finally emptied into the larger vial. If after shaking for fifteen seconds the color of the resulting homogeneous mixture remains purple-red, the oil is considered to be satisfactory". However, if the refrigeration oil contains a highly colored leak detector, the homogeneous mixture does not produce the expected test colors so that the kit is not suitable for such contaminated oils.

A field test kit of the two-phase type, identified as "UNI-KIT", consists of three vials and a glass ampoule containing potassium hydroxide solution. The largest vial has a capacity of approximately one fluid ounce and contains dried crystals of phenolphthalein indicator. When the ampoule is broken and its colorless contents emptied into the large vial with the aid of a small piece of rubber tubing for venting the ampoule and obtaining better drainage into the vial, as described in U.S. Pat. No. 3,653,839, the contents become pink. A second vial, containing isopropyl alcohol and toluene, is emptied into the mixture. Using the third vial for measurement, a sample of the refrigeration oil is then poured into the pink mixture, and the large vial is shaken vigorously. The resulting heterogeneous mixture frequently must stand for one to five minutes so that the partially emulsified layers can be separated sufficiently for an accurate color determination. Any pink color remaining in the bottom layer, even very light pink, signifies satisfactory oil. Therefore, if the oil in the top layer contains a leak detector, such as Dytel, which is even slightly miscible with or emulsified in the bottom layer, a slightly pinkish color is observed which could lead to an erroneous pass for an acidic refrigeration oil which is contaminated with the leak detector.

The fourth test kit, also of the two-phase type, is marketed as "PHASE II" and consists of a two-fluid ounce bottle, which is partially filled with a solvent solution consisting of benzene, methanol, and toluene, and a 0.5-fluid ounce bottle of neutralization solution. When the contents of the smaller bottle are poured into the large bottle, a purple-colored bottom layer is formed. The smaller bottle is then filled completely with oil to be tested and emptied into the larger bottle. After capping and shaking the larger bottle well, the mixture separates into two phases upon standing for two to three minutes. If the bottom layer loses its purple color, the sample has an acid number of 0.05 or more so that the oil should be replaced. This field test kit is probably the most convenient test kit which is now available for testing refrigeration oil taken from a system contaminated with a leak detector, even though it is subject to some interference from the dye. However, there are several practical drawbacks in that the kit requires the use of two bottles instead of only one bottle, considerable time is lost while waiting for phase separation, and benzene as one component of the solvent mixture is now a suspected carcinogen.

Other test kits of interest are described in U.S. Pat. No. 3,528,775 for determining the water content of water-immiscible petroleum products, U.S. Pat. No. 3,449,081 for performing blood tests, and U.S. Pat. No. 1,674,416 for testing alcohol.

In the refrigeration and air conditioning fields, no simple and quickly operated field test kit is known that is not obscured by a leak detector in the oil to be tested. Accordingly, an acid field test kit is needed that provides acidity indications that cannot be obscured by a leak detector in oil contaminated therewith, that requires minimum time for field testing, that requires only a single vial so that transferring liquids is not necessary, and that preferably contains no benzene.

SUMMARY OF THE INVENTION

It is therefore an object of this invention to provide an acid field test kit that is operable within a single bottle or vial for measuring a sample of a refrigeration oil, for carrying out the test precedure, and for obtaining reliable test results as to acidity of the oil.

It is also an object to provide an acid field test kit of the two-phase type wherein the phases separate with exceptional rapidity and without emulsification.

It is further an object to provide an acid field test kit having components that permit an acidity-related color change to be observed without interference from the color of a leak-detecting component of a refrigeration oil.

Therefore, in accordance with the objects and principles of this invention, an acid field test kit of the two-phase type is herein provided which comprises a single vial for storage of the testing solution, for measurement of the oil sample, and for carrying out the test procedure. The testing solution comprises an aqueous bottom layer, which includes a color indicator and which is highly ionic in nature, and a solvent top layer which preferably includes no benzene. In operation, this field test kit requires only one vial, provides fast phase separation, produces distinct colors, and utilizes cyclohexane as the preferred solvent. Fast phase separation into two distinct layers is effected by the highly ionic nature of the aqueous layer. With the test kit of this invention, the single vial is merely filled to the line on its neck and shaken. The layers separate almost immediately, and in a very short time the operator can detect the color of the bottom phase. If its color is blue to blue-green, the oil is satisfactory for further service. If its color is green to yellow-green, the oil is marginal for further use. If its color is distinctly yellow, the oil is bad and unquestionably should be changed.

The highly ionic nature of the aqueous layer is principally imparted by a water-soluble inorganic salt as a major component of the testing solution. This salt is preferably sodium chloride at 6-12% of an indicator stock solution by weight.

DESCRIPTION OF THE INVENTION

The method of preparing acid field test kits in general comprises the preparation of an indicator stock solution according to the following steps which are defined for an indicator, such as thymol blue, which changes color over a pH range of 8.0 to 9.6:

A. preparing a concentrated aqueous indicator solution;
B. preparing an indicator mixture comprising 20–28 percent by weight of a lower alcohol, 56–79 percent by weight of distilled water, 6–12 percent by weight of a water-soluble inorganic salt, and 0.2–0.3 percent by weight of the concentrated aqueous indicator solution;
C. adjusting the pH of the indicator mixture to 9.5 with 1.0 N alkaline hydroxide, preferably as a solution, to form an adjusted mixture;
D. adding to the adjusted mixture, to form the indicator stock solution, exactly the amount by weight of additional alkaline hydroxide solution so that the weight ratio of oil to be tested to one milliequivalent of the additional alkaline hydroxide is 1122; and
E. protecting the indicator stock solution with nitrogen.

Other materials producing an equivalent result can be substituted for the preferred materials. Indicators having a pH range of 8–10, such as phenolphthalein and phenol red, can be substituted for thymol blue to produce different colors. The term, alkaline hydroxide, includes potassium hydroxide, sodium hydroxide, and lithium hydroxide; potassium hydroxide is preferred. The term, water-soluble inorganic salt, includes sodium chloride, calcium chloride, magnesium chloride, sodium bromide, and like materials; sodium chloride is preferred.

Using KOH as the alkaline hydroxide in steps C and D on a gram basis, for example, so that one milliequivalent (meq.) is 0.0561 gram, the quantities used in step B are: 600 ml-900 ml of alcohol/meq. KOH, 1400–1950 ml of water/meq. KOH, 135–275 g NaCl/meq. KOH, and 5–7 ml of concentrated aqueous indicator solution/meq. KOH. The preferred levels, as outlined in Example 1 hereinafter, are 751 ml of alcohol/meq. KOH, 1690 ml of water/meq. KOH, 201 g of NaCl/meq. KOH and 6.4 ml of indicator solution/meq. KOH.

When KOH is used as a 1.000 N solution in step D, exactly 0.04018 percent by weight is added to the adjusted mixture to form the indicator stock solution.

Step C is necessary to neutralize any acidic components arising from the raw materials and to establish a baseline for the indicator which changes from yellow to blue over a pH range of 8.0 to 9.6. By setting the baseline at a pH of 9.5, the color is unmistakably blue. If an indicator such as phenol red had been chosen, the baseline would have been set at pH 8 since it changes from yellow to red over a range of 6.8 to 8.0.

The alkaline hydroxide added in step D is critical because the final kit should contain 0.775 mg KOH if KOH is the selected alkaline hydroxide. This amount represents the alkalinity consumed by 15.5 g of test oil with an acid number of 0.05. When properly filled with test solution and test oil, the weight of oil corresponds to 15.5 g. If the test oil is more acidic (acid number >0.05), the KOH is consumed and the kit changes color. If the oil has an acid number below 0.05, the oil does not consume all of the KOH and the kit remains blue.

In order to prepare kits of another size and be able to use larger or smaller oil samples, the amount of KOH in the kit would have to be adjusted so as to maintain a level of 20 g of oil/mg of KOH or 14.3 g of oil/mg of NaOH, for example. Whether the potassium hydroxide is added as a 1.0 N solution, or 2.0 N, etc., is not critical so long as the ratios are properly maintained.

The method further comprises the preparation of a plurality of test vials, each having a mark thereon to indicate a selected internal volume, according to the following steps:

A. adding to each test vial, while protecting its contents with nitrogen, a quantity of a waterimmiscible solvent equalling 22.7 percent of the volume, preferably principally comprising cyclic carbon compounds having no carboxyl groups, alcohol groups, or ether linkages in its side chains, such compounds including benzene, toluene, the xylenes, mesitylene, isopropyl benzene, and cyclohexane, and mixtures thereof; and B. adding to each test vial, while continuing to protect its contents with an inert gas such as nitrogen, a quantity of the indicator stock solution equalling 51.4 percent of the selected internal volume. The remaining capacity of each field test vial equals 25.9% of its total volumetric capacity up to the mark. One or more test vials are included in a field test kit to be used by automobile mechanics and air conditioning and refrigeration servicemen. When carrying out the test procedure in the field, the oil to be tested is filled to this mark, shaken, and allowed to settle and separate into two distinct phases. The color of the aqueous bottom phase is then examined to obtain the test results.

This procedure is illustrated with the following examples in which preferred materials and preferred quantities are used.

EXAMPLE 1

A plurality of acid field test kits were made according to the following preferred procedure, in which all bottles and vials were clean and dry and all vials had a capacity of two fluid ounces up to a mark thereon, as follows:

(1) a concentrated aqueous indicator solution was prepared by dissolving 2.0 g of thymol blue indicator, in two hundred ml. of distilled water;

(2) an indicator mixture was prepared under a nitrogen atmosphere by mixing 14.1 liters of isopropyl alcohol, 31.5 liters of distilled water, 3.175 kilograms of sodium chloride, and 120 ml. of the concentrated indicator solution;

(3) using a pH meter, the pH of the indicator mixture was adjusted to 9.5 with 1.0 N potassium hydroxide solution, using approximately 2.0–2.3 ml. of the KOH solution;

(4) 18.64 ml. of 1.000 N KOH was added to the indicator mixture to form the indicator stock solution which was thereafter protected with nitrogen;

(5) exactly 13.4 ml. of cyclohexane was charged to each field test kit vial;

(6) while protecting with nitrogen, exactly 30.4 ml. of the indicator stock solution was added to each vial containing cyclohexane, forming two phases of which the bottom layer of each kit was blue with the top layer varying from a slight yellow tint to clear; and (7) each vial was very carefully sealed.

EXAMPLE 2

Five samples of Suniso 3GS refrigeration oil were treated with oleic acid (Wilmar 110) to produce acid numbers of 0.02, 0.04 and 0.06. Dytel II leak detector was added in normal commercial quantities to each sample. (Suniso refrigeration oils, such as Suniso 3GS, 4 GS, and 5GS refrigeration oils, are naphthenic oils manufactured by the Sun Oil Co.). Five vials made according to Example 1 were filled with the oil samples. The test oil at acid number 0.02 produced a blue bottom layer, the test oil at 0.04 acid number produced a green bottom layer, and the test oil at 0.06 acid number, in triplicate, produced distinctly yellow bottom layers.

Other materials producing an equivalent result can be substituted for the preferred materials, such as toluene, benzene, and the xylenes being substituted for cyclohexane, and ethyl alcohol, n-propyl alcohol, and tert-butyl alcohol being substituted for isopropyl alcohol. The volumes and weight ratios of the water, cyclohexane, alcohol, and inorganic salt can be altered from the preferred amounts given hereinbefore without seriously affecting the test results.

Because it will be readily apparent to those skilled in the art that innumerable variations, modifications, applications, and extensions of these embodiments and principles can be made without departing from the spirit and scope of the invention, what is herein defined as such scope and is desired to be protected should be measured, and the invention should be limited, only by the following claims.

What is claimed is:

1. An acid field test kit for determining the acidity of oil samples, said test kit being of the two-phase type and operable within a single vial which has a selected internal volume, and said test kit being used: for measuring a sample of a refrigeration oil containing a highly colored leak detector; for carrying out a test procedure on said sample by fast phase separation into a solvent top layer and a highly ionic aqueous bottom layer; and for obtaining reliable test results as to acidity of said oil; and said test kit comprising:

A. at least one said vial having a means for indicating said selected internal volume;

B. a water-immiscible solvent, which is disposed within said vial; and

C. an indicator stock solution which is disposed within said vial, comprising:

(1) 20–28% by weight of a lower alcohol, (2) 56–79% by weight of water, (3) 6–12% by weight of a water-soluble inorganic salt, (4) 0.2–0.3% by weight of a concentrated aqueous solution of a selected indicator having an unmistakable first color at a selected baseline pH which is at about the alkaline limit of the pH range for said indicator, (5) sufficient alkaline hydroxide solution to create said baseline pH, and (6) an amount of alkaline hydroxide solution which permits an unmistakable selected second color to appear within said aqueous bottom layer only when the acid number of said oil sample exceeds about 0.05 by limiting the change in pH from said baseline pH to a selected acidic pH at about the acid limit of said pH range after said oil sample has been mixed within said vial with said water-immiscible solvent and said indicator stock solution.

2. The acid field test kit of claim 1, wherein said indicator is phenol red.

3. The acid field test kit of claim 1, wherein said indicator stock solution occupies 51.4% of said selected internal volume, said indicator is thymol blue, and the weight ratio of said oil sample to one milliequivalent of said alkaline hydroxide is 1122.

4. The acid field test kit of claim 3, wherein said selected internal volume is about two fluid ounces.

5. The acid field test kit of claim 3, wherein the ratio in milliliters of said water to one milliequivalent of said alkaline hydroxide is 1400-1950.

6. The acid field test kit of claim 5, wherein said water to alkali hydroxide ratio is 1690.

7. The acid field test kit of claim 3, wherein said alkaline hydroxide is selected from the group consisting of potassium hydroxide, sodium hydroxide, and lithium hydroxide.

8. The acid field test kit of claim 7 which comprises 0.775 mg. of potassium hydroxide.

9. The acid field test kit of claim 3, wherein said water-soluble inorganic salt is selected from the group consisting of sodium chloride, calcium chloride, magnesium chloride, and sodium bromide.

10. The acid field test kit of claim 9, wherein said water-soluble inorganic salt is sodium chloride and the weight ratio in grams of said sodium chloride to one milliequivalent of said alkaline hydroxide is 135-275.

11. The acid field test kit of claim 10, wherein said weight ratio of sodium chloride to alkaline hydroxide is 201.

12. The acid field test kit of claim 11, wherein the ratio in milliliters of said alcohol to one milliequivalent of said alkaline hydroxide is 600-900.

13. The acid field test kit of claim 12, wherein said alcohol to alkaline hydroxide ratio is 751.

14. The acid field test kit of claim 3, wherein said water-immiscible solvent occupies exactly 22.7% of said selected internal volume.

15. The acid field test kit of claim 14, wherein said water-immiscible solvent principally comprises cyclic carbon compounds having no carboxyl groups, alcohol groups, or ether linkages in the side chains.

16. The acid field test kit of claim 15, wherein said cyclic compounds are selected from the group consisting of benzene, toluene, the xylenes, mesitylene, isopropyl benzene, and cyclohexane.

17. The acid field test kit of claim 16, wherein said cyclic compound is cyclohexane.

18. The acid field test kit of claim 17, wherein said indicator stock solution comprises, on a weight basis: 23.86% of isopropanol as said lower alcohol, 67.78% of water, 8.08% of sodium chloride as said water-soluble inorganic salt, and 0.26% of said concentrated aqueous indicator solution.

19. The acid field test kit of claim 18, wherein said concentrated aqueous indicator solution contains 1.0% by weight of thymol blue indicator.

20. The acid field test kit of claim 19, wherein the contents of said vial are protected with nitrogen.

21. The acid field test kit of claim 19, wherein, after filling said vial with said sample of a refrigeration oil so that said selected internal volume is fully utilized and shaking, a two-phase mixture is obtained in which said bottom layer is blue when said refrigeration oil has an acid number of 0.02, green when said refrigeration oil has an acid number of 0.04, and distinctly yellow when said refrigeration oil has an acid number of 0.06.

22. The process of assembling an acid field test kit for determining acidity of refrigeration oil samples, comprising:

A. dissolving a pH indicator, having a pH range of about 8-10, in distilled water to form a concentrated aqueous indicator solution;

B. preparing an indicator stock solution under an inert gas atmosphere by the following steps:
 (1) preparing an indicator mixture by mixing 20-28% by weight of a lower alcohol, 56-79% by weight of distilled water, 6-12% by weight of a water-soluble inorganic salt, and 0.2-0.3% by weight of said concentrated aqueous indicator solution;
 (2) using a pH meter, adjusting the pH of said indicator mixture to 9.5 by adding 1.0 N alkaline hydroxide solution to said indicator mixture to form an adjusted mixture;
 (3) adding to said adjusted mixture, to form said indicator stock solution, exactly the amount of additional alkaline hydroxide solution that the weight ratio of oil to be tested to one milliequivalent of said additional alkaline hydroxide is 1122; and C. preparing a plurality of test kit vials, each vial having a mark thereon to indicate a selected internal volume, by the following steps while protecting the contents thereof with an inert gas:
 (1) adding to said each vial a quantity of a water-immiscible solvent equalling 22.7 percent of said selected internal volume, and
 (2) adding to said each vial a quantity of said indicator stock solution equalling 51.4 percent of said selected internal volume, said oil to be tested in each said test kit vial being obtained from said refrigeration oil samples and being added within said selected internal volume up to said mark.

23. The process of claim 22, wherein said alkaline hydroxide is potassium hydroxide.

24. The process of claim 22, wherein said concentrated aqueous indicator solution contains 1.0% by weight of thymol blue as said pH indicator.

25. The process of claim 24, wherein 0.26% by weight of said thymol blue solution is added for preparing said indicator mixture.

26. The process of claim 22, wherein said lower alcohol is isopropanol.

27. The process of claim 26, wherein said isopropanol is 23.86% by weight of said indicator stock solution.

28. The process of claim 22, wherein said soluble inorganic salt is sodium chloride.

29. The process of claim 28, wherein said sodium chloride is 8.08% by weight of said indicator stock solution.

* * * * *